(12) United States Patent
Grund et al.

(10) Patent No.: US 7,235,704 B2
(45) Date of Patent: Jun. 26, 2007

(54) PROCESS FOR PREPARING ISOBUTENE FROM TERT-BUTANOL

(75) Inventors: Gerda Grund, Duelmen (DE); Wilfried Bueschken, Haltern am See (DE); Dieter Reusch, Marl (DE); Andreas Beckmann, Recklinghausen (DE)

(73) Assignee: Oxeno Olefinchemie GmbH, Marl (DE)

( * ) Notice: Subject to any disclaimer, the term of this patent is extended or adjusted under 35 U.S.C. 154(b) by 386 days.

(21) Appl. No.: 10/868,904

(22) Filed: Jun. 17, 2004

(65) Prior Publication Data

US 2005/0014985 A1 Jan. 20, 2005

(30) Foreign Application Priority Data

Jun. 17, 2003 (DE) ................. 103 27 215

(51) Int. Cl.
*C07C 1/00* (2006.01)
(52) U.S. Cl. ..................... 585/639; 585/638
(58) Field of Classification Search ......... 585/638–640
See application file for complete search history.

(56) References Cited

U.S. PATENT DOCUMENTS 3,665,048 A   5/1972   Grane et al.
4,208,540 A   6/1980   Imaizumi et al.
4,423,271 A   12/1983  Obenaus et al.
5,518,699 A   5/1996   Kashnitz et al.
2004/0171891 A1  9/2004  Scholz et al.

FOREIGN PATENT DOCUMENTS

| DE | 29 13 796 | 10/1979 |
|---|---|---|
| DE | 29 53 583 | 4/1981 |
| DE | 31 51 446 | 7/1983 |
| DE | 199 36 675 | 7/2001 |
| EP | 0 255 948 | 2/1988 |
| GB | 2 022 129 | 12/1979 |
| WO | WO 93/21139 | 10/1993 |

OTHER PUBLICATIONS

U.S. Appl. No. 10/534,973, filed May 16, 2005, Reusch, et al.
U.S. Appl. No. 10/526,763, filed Mar. 7, 2005, Reusch, et al.

*Primary Examiner*—Glenn Caldarola
*Assistant Examiner*—In Suk Bullock
(74) *Attorney, Agent, or Firm*—Oblon, Spivak, McClelland, Maier & Neustadt, P.C.

(57) ABSTRACT

Isobutene is prepared by dissociating tert-butanol into isobutene and water over an acid ion-exchange resin arranged as a fixed bed in at least one reactor at a temperature of from 80 to 150° C. and at a pressure of from 5 to 25 bar to obtain a reaction mixture, separating the reaction mixture into isobutene, a by-product, water and at least one mixture of undissociated tert-butanol and water. The reactor is operated pseudo-isothermally, with a temperature difference between inflowing and outflowing streams of less than 15 K.

20 Claims, 4 Drawing Sheets

PROCESS FOR PREPARING ISOBUTENE FROM TERT-BUTANOL

BACKGROUND OF THE INVENTION

1. Field of the Invention

The present invention relates to a process for preparing isobutene by dissociation of tert-butanol (TBA) over acid ion-exchange resins.

2. Discussion of the Background

Isobutene is a starting material for the production of butyl rubber, polyisobutylene, isobutene oligomers, branched $C_5$-aldehydes and $C_5$-carboxylic acids. It is also used as alkylating agent and as intermediate for producing peroxides.

In industrial streams, isobutene occurs together with saturated and unsaturated $C_4$-hydrocarbons. Owing to the small boiling point difference and the very low separation factor between isobutene and 1-butene, isobutene cannot be separated economically from these mixtures by distillation. For this reason, isobutene is isolated from industrial hydrocarbon mixtures by converting isobutene into a derivative which can easily be separated off from the remaining hydrocarbon mixture and then redissociating the isolated derivative to form isobutene and the derivative-forming agent.

Isobutene is usually separated from $C_4$ fractions, for example the $C_4$ fraction from a steam cracker, in the following way. After the major part of the multiply unsaturated hydrocarbons, mainly butadiene, has been removed by extraction (or extractive distillation) or selective hydrogenation to linear butenes, the remaining mixture (raffinate I or hydrogenated cracked $C_4$) is reacted with an alcohol or water. When methanol is used, methyl tert-butyl ether (MTBE) is formed from isobutene, and when water is used, tert-butanol (TBA) is formed. After they have been separated off, both products can be dissociated to form isobutene in a reversal of their formation.

The dissociation of TBA can be carried out more easily than that of MTBE and gives a smaller amount of by-products. The acid-catalyzed dissociation of TBA to give isobutene of high purity is known. This dissociation can be carried out in the liquid or gas phase.

The dehydration of TBA in the gas phase is carried out over acidic aluminosilicate catalysts, for example as described in EP 0 255 948, or over aluminum oxides, for example as described in U.S. Pat. No. 3,665,048, or over zeolites, for example as described in WO 93/21139. A disadvantage of these processes is that, owing to the high temperatures and high isobutene concentrations inherent in the process, by-products are formed by dimerization or oligomerization of the isobutene formed. Attempts have been made to minimize these secondary reactions by reducing the isobutene concentration in the gaseous starting material by addition of inert gas. This results in an additional process step.

A number of processes are known for the dehydration of TBA in the liquid phase. In DE 29 53 583, the dehydration of TBA is carried out in a column whose lower part is packed with packing elements and whose upper part is filled with an acid ion-exchange resin. An aqueous TBA solution is fed continuously into the column just below the ion-exchange resin. An isobutene-stream is obtained as overhead product and is rectified in a further column to give isobutene having a purity of 99.95%. The TBA conversion is 99%. The isobutene yield is not disclosed.

In DE 29 13 796, the dissociation of TBA is carried out in a pressure range from 5 to 7 bar and a temperature range from 110 to 120° C. in a stirred vessel in which an acid ion-exchange resin is suspended in a solution of TBA and water. A mixture of water and TBA is passed in gaseous form into the liquid phase in this reactor. At the top of the reactor, a gaseous mixture comprising isobutene, TBA and water is obtained. At the bottom outlet, a liquid mixture comprising water, TBA and by-products is taken off under level control. The overhead product is separated by distillation into isobutene and a mixture of water and TBA, which is returned to the reactor. The phase taken off from the reactor in liquid form is separated in at least two columns into water, by-products such as oligomers of isobutene and TBA which is recirculated to the reactor. Apart from the complexity of the plant, a further disadvantage is that the catalyst is damaged by the mechanical stress, which results in a short operating life.

In DE 31 51 446, the redissociation of TBA into isobutene and water is carried out in a homogeneous and liquid phase at temperatures of from 80° C. to 150° C. and pressures of from 5 to 25 bar over a strong acid ion-exchange resin present in a fixed bed, and the homogeneous, liquid reaction product mixture is separated in one or more columns into isobutene, by-products, water and a water/TBA mixture which is recirculated to the reactor. In this process, the amount of water present in the total TBA recirculated to the reactor is greater than that which corresponds to the tert-butanol/water azeotrope. As a result of the recirculation of a large amount of water, the space-time yield of the process is not particularly high and a high energy input is necessary for the materials separation. In addition, the large amounts of circulating material require a very large outlay in terms of equipment or correspondingly large dimensions of the apparatuses.

SUMMARY OF THE INVENTION

Since the known processes are not satisfactory in terms of selectivity, space-time yield, energy consumption and/or capital costs, it is an object of the present invention to develop a process which does not have these disadvantages.

This and other objects have been achieved by the present invention the first embodiment of which includes a process for preparing isobutene, comprising:

dissociating tert-butanol into isobutene and water over an acid ion-exchange resin arranged as a fixed bed in at least one reactor at a temperature of from 80 to 150° C. and at a pressure of from 5 to 25 bar to obtain a reaction mixture, separating the reaction mixture into isobutene, a by-product, water and at least one mixture of undissociated tert-butanol and water;

wherein the reactor is operated pseudo-isothermally, with a temperature difference between inflowing and outflowing streams of less than 15 K.

In another embodiment, the present invention relates to a reactor system for carrying out equilibrium reactions isothermally in the liquid phase over a fixed-bed catalyst, comprising:

at least two physically separate reaction zones which each have a catalyst arranged in a fixed bed and facilities for maintaining isothermal operation;

wherein between each two reaction zones there is a separation zone having means for bringing at least part of at least one of the products of the equilibrium reaction into the gas phase by changing the pressure or temperature, separating it off from the reaction mixture and discharging it from the reactor and for transferring the remaining reaction mixture to the following reaction zone, optionally, a further means setting the temperature or pressure in the subsequent reaction zone to precisely the value in the preceding reaction zone.

DETAILED DESCRIPTION OF THE INVENTION

Figure 1:
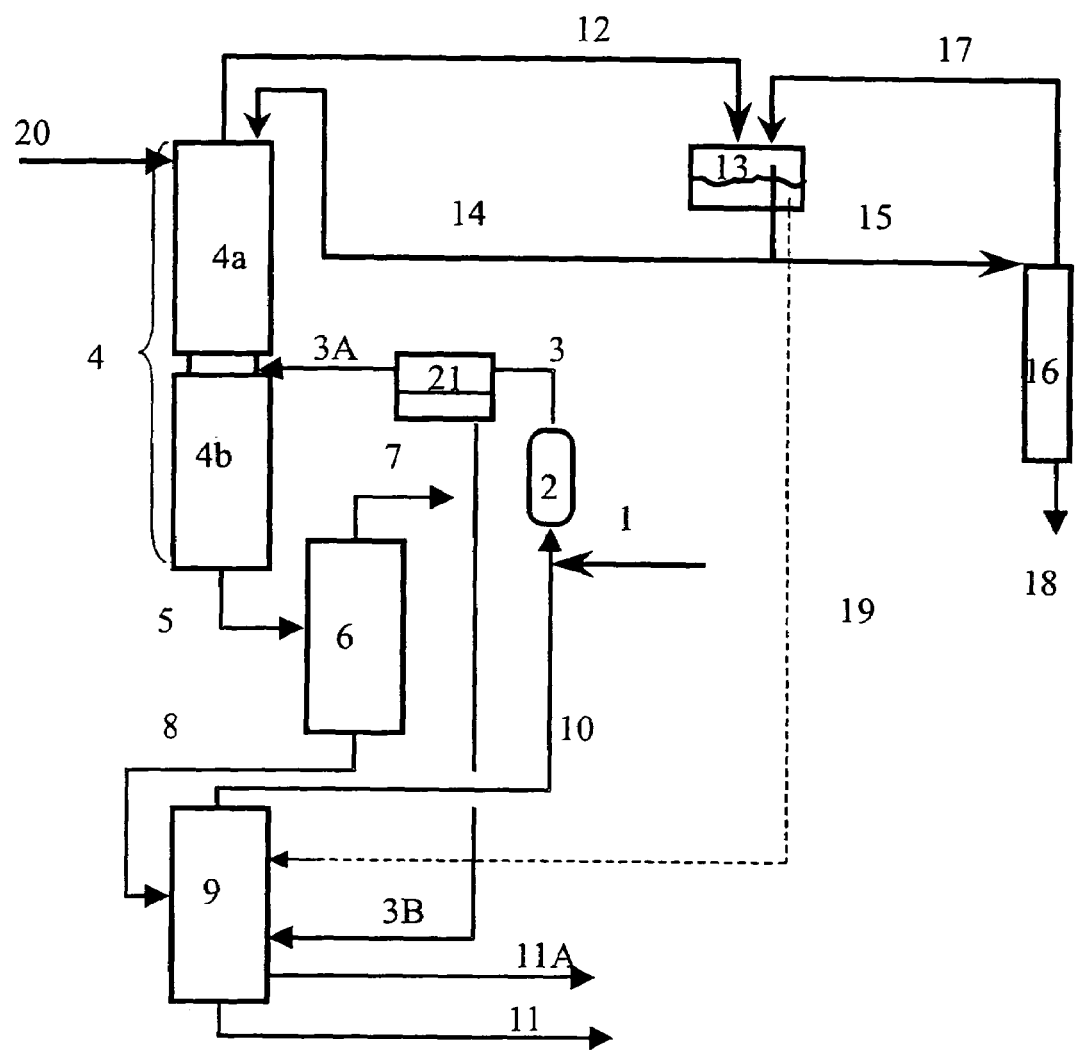
FIG. 1 shows a block diagram of a plant in which the process of the present invention can be carried out.

It has now surprisingly been found that the recycle ratio and thus the equipment requirements and the energy consumption for the formation of isobutene from tert-butanol can be reduced by the reactor in which the dissociation is carried out being operated isothermally or at least pseudo-isothermally.

The present invention accordingly provides a process for preparing isobutene by dissociation of tert-butanol into isobutene and water over a strong acid ion-exchange resin arranged as a fixed bed in at least one reactor. The reaction proceeds preferably at a temperature of from 80 to 150° C. and a pressure of from 5 to 25 bar. Subsequently the reaction mixture is separated into isobutene, by-products, water and at least one mixture of undissociated tertiary butanol and water. The reactor is operated pseudo-isothermally, i.e. the difference in the temperatures of the inflowing and outflowing streams (feed stream and product stream) is less than 15 K, preferably less than 10 K and particularly preferably less than 5 K and very particularly preferably less than 1 K. The feed to the reactor comprises fresh feed stream and one or more recycle streams which comprise a mixture of undissociated tert-butanol and water. The mass ratio of fresh feed stream to the sum of the recycle streams is less than 1:10, preferably less than 1:5 and very particularly preferably less than 1:3. The mass ratio of fresh feed stream to the turn of the recycle stream includes all values and subvalues therebetween, especially including 1:1, 1:2, 1:3, 1:4, 1:5, 1:6, 1:7, 1:8 and 1:9. The reaction temperature includes all values and subvalues therebetween, especially including 90, 100, 110, 120, 130 and 140° C. The reaction pressure includes all values and subvalues therebetween, especially including 6, 8, 10, 12, 14, 16, 18, 20, 22 and 24 bar. The difference in temperatures of inflowing and outflowing streams includes all values and subvalues therebetween, especially including 0, 0.5, 1, 2, 3, 4, 5, 6, 7, 8, 9, 10, 11, 12, 13 and 14K.

The present invention likewise provides isobutene prepared by the process of the invention.

The present invention further provides a reactor system for carrying out equilibrium reactions isothermally in the liquid phase over fixed-bed catalysts, where at least one of the reaction products is partly, preferably predominantly, present in gaseous form under temperature and pressure conditions under which all starting materials and at least one reaction product are predominantly present in liquid form. In particular, the present invention provides a reactor system for carrying out the process of the invention, wherein the reactor system has at least two physically separate reaction zones which each have a catalyst arranged in a fixed bed and facilities for maintaining isothermal operation. Between each two reaction zones there is a separation zone having means for bringing at least part of at least one of the products of the equilibrium reaction into the gas phase by changing the pressure or temperature, separating it off from the reaction mixture and discharging it from the reactor. In addition, the separation zone has means for transferring the remaining reaction mixture to the following reaction zone. There is a further means which allows the temperature or pressure in the subsequent reaction zone to be set to precisely the value in the preceding reaction zone, present if desired. This reactor or this reactor system can be utilized, in particular, for carrying out endothermic reactions, for example the dissociation of tertiary ethers to form the corresponding isoolefins and alcohols.

The process of the present invention makes it possible to carry out the dissociation of tert-butanol with significantly smaller mass flows, in particular smaller amounts of circulated material, while maintaining the same high selectivity. In this way, the energy consumption and the dimensions of the apparatuses can be reduced compared to conventional processes.

It is possible to carry out the dissociation beyond the equilibrium carrying out the process in a specific type of apparatus in which a plurality of reactors or reaction zones are connected in series and a separation zone in which isobutene is vaporized and separated off in gaseous form from the reaction mixture is present between each of these reaction zones. In this case, part of the isobutene is removed from the equilibrium in the separation zones.

The removal of water from the reactor output or from other water-containing streams by a membrane employed in the TBA dissociation in the preferred variant of the process of the present invention allows the mass flows to be treated to be reduced further. In this way, the conversions per path through the reactor can be increased further.

It can be advantageous to use a plurality of reactors which are connected in series or in parallel, with preference being given to all reactors being operated isothermally. It is possible to use various types of reactor in which ion-exchange resin can be present as a fixed bed, for example fixed-bed reactors, shell-and-tube reactors or reactors of other types. The reactors are equipped to allow for isothermal operation, i.e. for the removal or introduction of heat, by using for example heat exchangers. The reactor(s) is/are operated pseudo-isothermally, i.e. the difference in the temperatures of the inflowing and outflowing streams (feed stream and product stream) is less than 15 K, preferably less than 10 K, preferably in a single path and the flow through them can be from the top downward or vice versa.

The reaction temperature in the dissociation reactor(s) is preferably in the range from 80° C. to 150° C., more preferably in the range from 100° C. to 130° C., in the process of the present invention. When a plurality of reactors are used, the temperatures can be identical or different.

The reaction pressure in the dissociation reactor or reactors is from 5 to 25 bar, with the pressure being selected so as to be sufficiently high for the isobutene formed in the reactors or in the reaction zones of the reactors to remain virtually completely and essentially homogeneously dissolved in the reaction mixture without formation of a gas phase. In general, it is advantageous for the pressure in the dissociation reactor to be greater than the column pressure at the feed points of a column installed downstream of the reactor or the last reactor of a reactor cascade to separate the isobutene obtained from the product stream, because the expansion vaporization can then be utilized to aid the removal of isobutene and a pump can be dispensed with.

The process is preferably carried out in one or more reactors in which a particulate acidic ion exchanger is present as catalyst in a fixed bed.

A preferred group of acid ion-exchange resins used as catalysts comprises solid ion-exchange resins bearing sulfonic acid groups. Examples of suitable ion-exchange resins are those which are prepared by sulfonation of phenol-aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. Particular preference is given to using the cooligomers formed by reaction of styrene with divinylbenzene as precursors for preparing ion-exchange resins bearing sulfonic acid groups. The resins can be produced as gels, in macroporous form or in sponge form. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, Lewatit K2611, Lewatit K2631, OC 1501, Lewatit K2671, Lewatit K2629, Lewatit K2431.

The properties of these resins, in particular specific surface area, porosity, stability, swelling or shrinkage and ion-exchange capacity, can be varied by the production process.

Commercial, macroporous cation exchangers which have been modified by partial ion exchange or by thermal desulfonation can also be used if desired.

In the process of the present invention, the ion-exchange resins are preferably used in their H form. The ion-exchange capacity is preferably from 2 to 7 eq/kg, in particular from 3 to 6 eq/kg (based on moist commercial resin). The ion-exchange capacity includes all values and subvalues therebetween, especially including 2.5, 3, 3.5, 4, 4.5, 5, 5.5, 6 and 6.5 eq/kg.

Particular preference is given to using macroporous resins, for example Lewatit SCP 118, Lewatit SCP 108, Lewatit K2631, Amberlyst 15 or Amberlyst 35. The ion-exchange resins can be used as shaped bodies such as cylinders, rings or spheres if desired.

The particle size of industrial resins is generally in the range from 0.5 to 2 mm. The particle size of the industrial resins includes all values and subvalues therebetween, especially including 0.6, 0.8, 1, 1.2, 1.4, 1.6 and 1.8 mm. However, the particle size distribution chosen can also be narrower or broader. Thus, for example, ion-exchange resins having a very uniform particle size (monodisperse resins) can also be used.

It can be advantageous to use larger particles in reactors through which the reaction mixture flows at high linear velocities, so as to reduce the differential pressure, and to use smaller particles in reactors through which the reaction mixture flows at a low linear velocity, so as to achieve optimum conversion.

When using a plurality of reactors, these can be charged with resins of identical or different particle size (or particle size distribution) or with different or identical shaped bodies.

To prevent the resins from eliminating acid groups during operation, which could cause problems in the work-up section of the process, and to maintain a high catalyst activity over a very long period of time, the ion-exchange resin can be pretreated, for example by rinsing with water, the TBA or TBA/water mixtures. Rinsing is preferably carried out at a temperature of from 40 to 120° C. The rinsing temperature includes all values and subvalues therebetween, especially including 50, 60, 70, 80, 90, 100 and 110° C.

Since the conversion in the reactor is usually limited by the chemical equilibrium and/or the miscibility gap, it is often necessary to use large circulating streams in order to achieve virtually complete dissociation of the TBA in a plant. To keep the amount of circulating material in the work-up of the reactor output as small as possible or to reduce it, it is advantageous to employ particular types of reactors or reactor systems which allow a mode of operation which avoids these disadvantages. The process is therefore particularly preferably carried out with the dissociation being carried out (virtually) to the equilibrium of the dissociation reaction in a first reaction zone, isobutene being separated off in gaseous form in a subsequent separation zone and the dissociation being continued (virtually) to the equilibrium of the dissociation reaction in a subsequent reaction zone. If further separation zones and reaction zones are present, these process steps are repeated the appropriate number of times. As a result of this measure, the dissociation reaction proceeds not only to a one-off establishment of equilibrium but instead the reaction can be carried out a number of times, depending on the number of separation zones, to establishment of the reaction equilibrium. In this way, more complete dissociation is achieved in a single pass of the reaction mixture through the reactor or the reactor system than is achieved in conventional reactors or reactor systems.

The above mentioned mode of operation can be achieved in various ways. Thus, for example, it can be advantageous in the process of the present invention to use at least one reactor having at least two reaction zones which each have a strong acid ion-exchange resin arranged as a fixed bed, where between each two reaction zones there is a separation zone in which at least part of one of the products of the dissociation is separated off from the reaction mixture by bringing it (partly) into the gas phase and is discharged from the reactor. In each of the reaction zones, there are means, e.g. heatable plates or tubes, which enable isothermal operation to be achieved at least in the reaction zones. The pressure and the temperature in the reaction zones of the reactor are preferably chosen so that the reaction mixture is present in the liquid phase. The pressure and the temperature in the separation zones are preferably chosen so that at least part of the isobutene is present in the gas phase.

Figure 2:
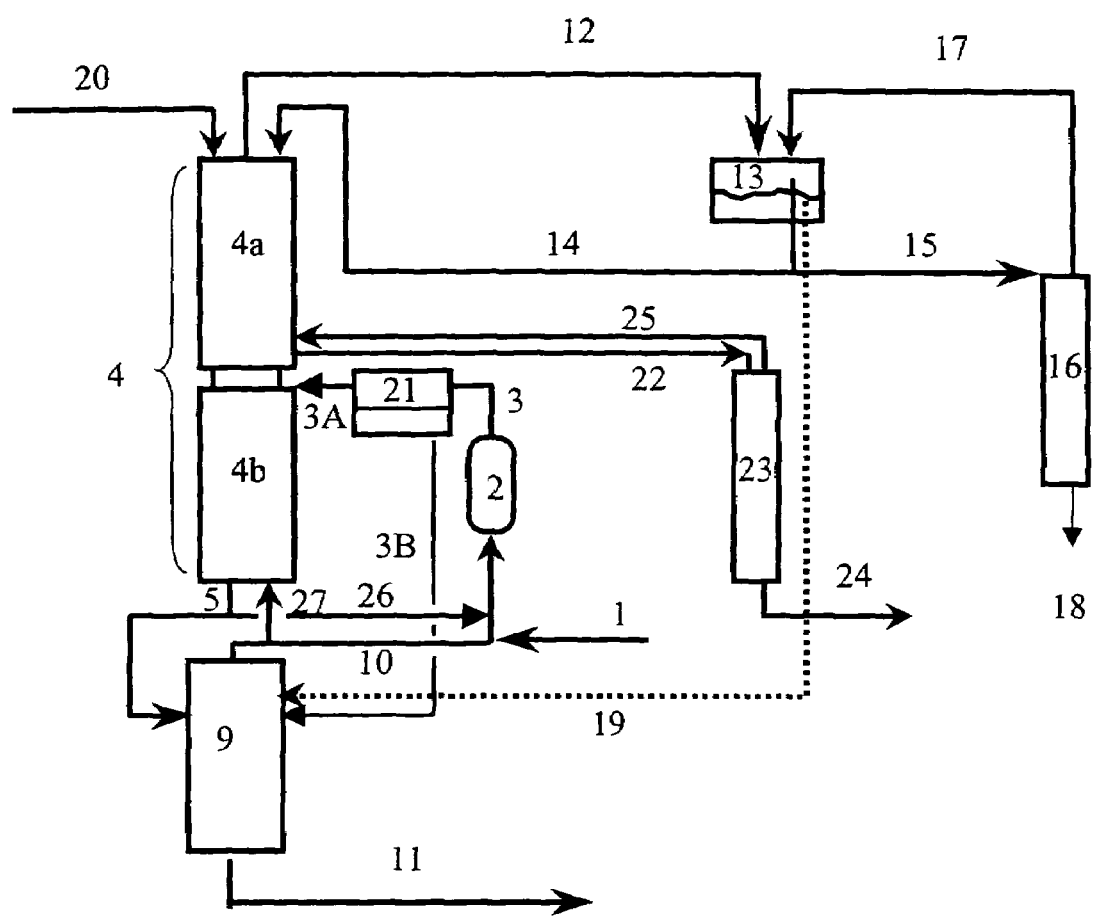
FIG. 2 shows a block diagram of a plant in which the process of the present invention can be carried out.
Figure 3:
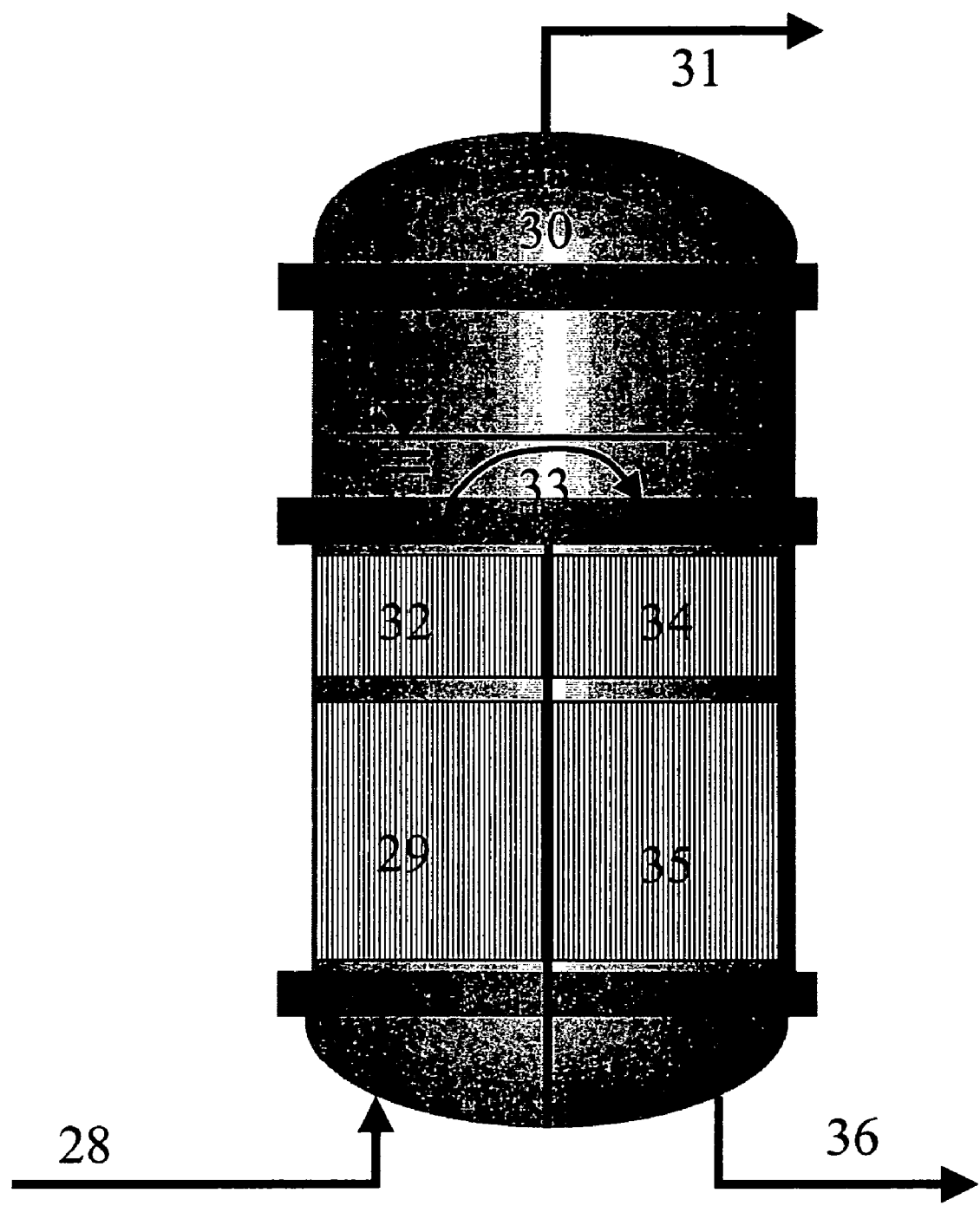
FIG. 3 shows the structure of a reactor according to the present invention.

FIG. 3 shows the structure of such a particular reactor. The reactor feed (28) is fed from below into the reactor and passed into the first reaction region (29). There, catalyst is located in heatable tubes or other heatable intermediate spaces. The reaction which occurs forms isobutene and water to a maximum extent limited by chemical equilibrium being reached. When an appropriate operation pressure in the reactor is chosen, part of the isobutene vaporizes and forms a vapor phase (30), which can, as product stream (31), be passed directly to column (4) of FIG. 1 or 2. The vaporization of the isobutene can be additionally reinforced by an optional heating matrix (32). The liquid phase (33) can be brought back to the permissible reaction temperature by a further heat-exchange element (34) before it is passed into the second reaction region (35) which is, like the first reaction region (29), charged with catalyst and can be heated. There, the reaction continues to a maximum extent limited by the chemical equilibrium. The reaction regions (29) and (35) are physically separate from one another as a result of the reactor construction. The substreams (36) and (31) leaving the reactor correspond in total to the stream (3)

in FIGS. 1 and 2. While stream (31) is fed directly into the column (4), stream (36) can, as shown in FIGS. 1 and 2, firstly be depleted in water by a separation unit (21) and then be introduced into column (4) or can also be fed directly into the column.

Figure 4:
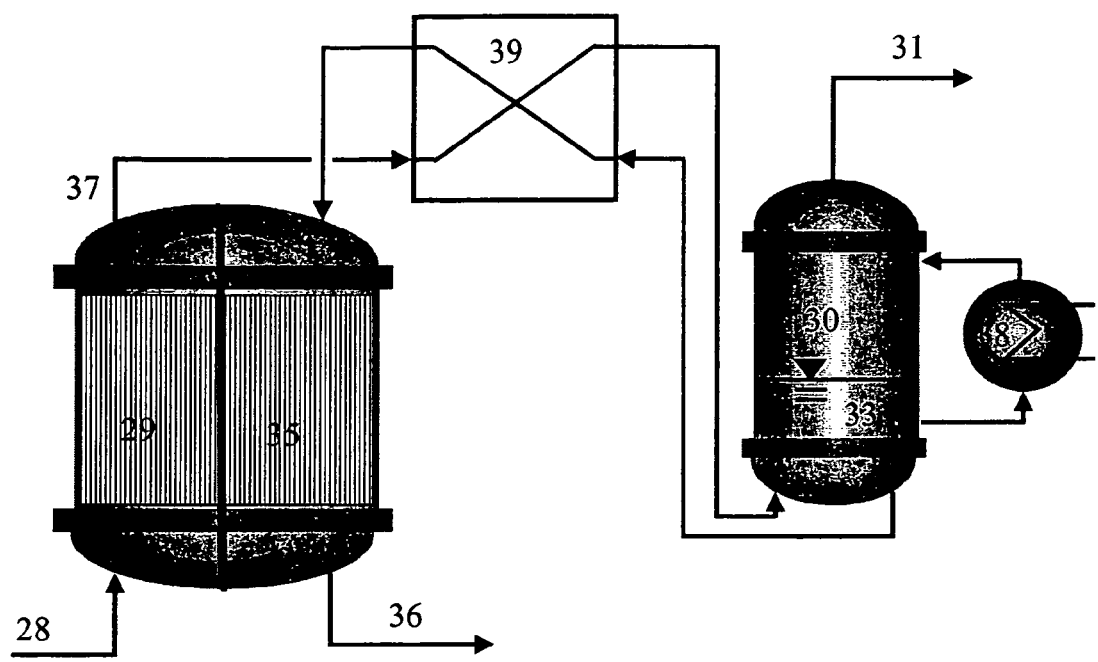
FIG. 4 shows the structure of a reactor system in which the process of the present invention can be carried out.

A different construction of such a reactor is shown in FIG. 4. The reactor feed (28) is fed into the reactor once again from the bottom in a manner analogous to FIG. 3 or alternatively from the top and passed into the first reaction region (29). There, catalyst is located in heatable tubes or other heatable intermediate spaces. The reaction which occurs forms isobutene and water to a maximum extent limited by chemical equilibrium being reached. The operating pressure of the reaction is chosen so as to be sufficiently high for no vaporization to occur in the reactor. The reactor output (37) is fed into a vessel with vaporizer or directly into a vaporizer and forms, as a result of the introduction of heat by the heating element or vaporizer (38), a vapor phase (30) which can be passed, as product stream (31), directly into a column for work-up, e.g. into column (4) of FIG. 1 or 2. The liquid phase (33) can be brought back to the permissible reaction temperature by a heat-exchange element (39) and thus preheat the stream (37) in order to save energy before it is passed to the second reaction region (35) which, like the first reaction region (29) is charged with catalyst and can be heated. There, the reaction continues to a maximum extent limited by the chemical equilibrium. The reaction regions (29) and (35) are physically separate from one another as a result of the reactor construction. This type of construction is simple to achieve in engineering terms. As an alternative, the reaction mixture can flow through the two reaction regions of the reactor in cocurrent from the bottom upward or from the top downward. The substreams (36) and (31) leaving the reactor correspond in total to the stream (3) in FIGS. 1 and 2. While stream (31) is fed directly into the column (4), stream (36) can, as shown in FIGS. 1 and 2, firstly be depleted in water by a separation unit (21) and then be introduced into column (4) or can also be fed directly into the column.

However, this mode of operation can also be achieved by the process being carried out in at least two reactors and the liquid reactor output from the first reactor being transferred to a zone in which part of the reactor output is brought into a gas phase by changing the pressure and/or temperature and thus being separated off from the liquid phase and the liquid phase being passed to the second reactor. This intermediate vaporization in the two-stage or multistage reactor system can be carried out by, for example, reducing the pressure to below the reaction pressure. It can be advantageous, in the case of vaporization in a two-stage or multistage reactor system, for heat exchange between the liquid stream fed to vaporization and the liquid stream returned from vaporization to be carried out. Heat losses can be avoided in this way.

Figure 5:
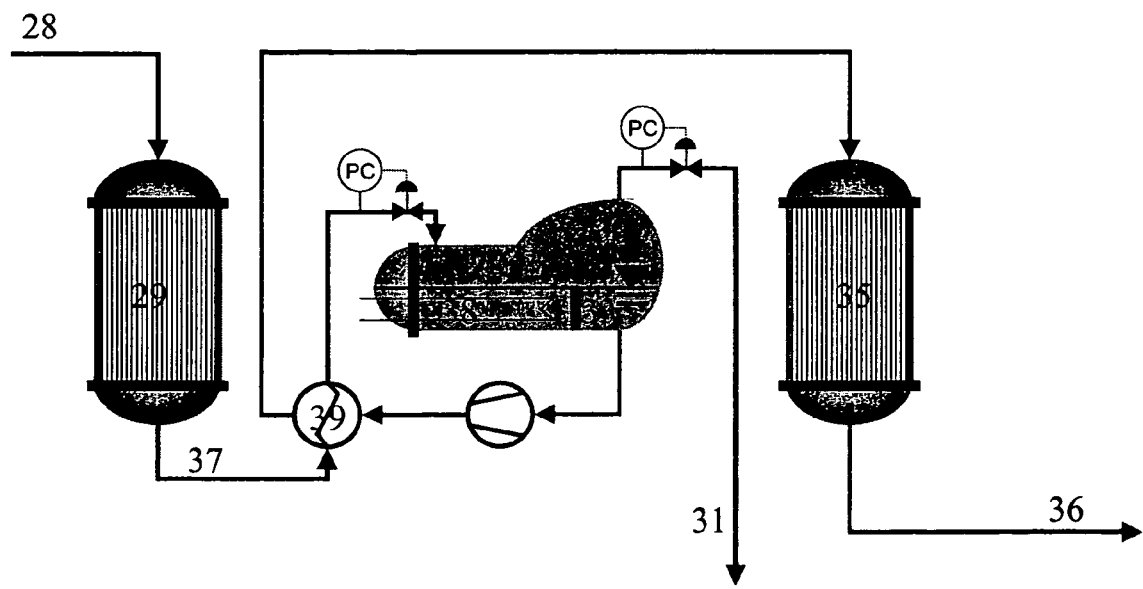
FIG. 5 shows a block diagram of a plant in which the process of the present invention can be carried out.

This procedure requires no complicated apparatuses and the apparatus costs for the reactor system can be kept low. An appropriate system is shown in FIG. 5. The reactor feed (28) is fed into the first reaction region (29) in a manner analogous to FIG. 4. This reaction region comprises one or more reactors in which the catalyst is located in heatable tubes or other heatable intermediate spaces. The flow through the reactor(s) can be from the top downward or vice versa. The reaction which occurs forms isobutene and water to a maximum extent limited by chemical equilibrium being reached. The operating pressure of the reactor is chosen so as to be sufficiently high for no vaporization to occur in the reactor. The reactor output (37) is fed into a vessel with vaporizer or directly into a vaporizer, preferably a kettle vaporizer, and forms, as a result of the introduction of heat by the heating element or vaporizer (38), a vapor phase (30) which can be passed, as product stream (31), directly into a column for work-up, e.g. into column (4) of FIG. 1 or 2. PC in FIG. 5 refers to a pressure control which can be used to decrease the operating pressure of vaporizer (38). Vaporization can also be aided by reducing the operating pressure of the vaporizer. In this way, the product is less strongly superheated than in the above-described construction types. The liquid phase (33) can be brought back to the permissible reaction temperature by a heat-exchange element (39) and thus preheat the stream (37) in order to save energy before it is passed to the second reaction region (35) which, like the first reaction region (29) configured as a single reactor or a plurality of reactors and is charged with catalyst and can be heated. There, the reaction continues to a maximum extent limited by the chemical equilibrium. The substreams (36) and (31) leaving the reactor correspond in total to the stream (3) in FIGS. 1 and 2. While stream (31) is fed directly into the column (4), stream (36) can, as shown in FIGS. 1 and 2, firstly be depleted in water by a separation unit (21) and then be introduced into column (4) or can also be fed directly into the column.

The mass fraction of vapor which is generated in the reactors of FIG. 3 to 5 and is passed as stream (31) into a work-up column, for example column (4) of FIG. 1 or 2, is preferably from 1 to 80% by mass, more preferably from 5 to 75% by mass, of the feed stream (28). The mass fraction of vapor includes all values and subvalues therebetween, especially including 10, 15, 20, 25, 30, 35, 40, 45, 50, 55, 60, 65 and 70% by mass, of the feed stream (28).

The process of the present invention allows tert-butanol (TBA) to be dissociated into isobutene and water. In the process of the present invention, it is possible to use either technical-grade TBA contaminated with oligomers of isobutene, for example diisobutene, or pure TBA. Preference is given to using TBA/water mixtures, for example TBA/water azeotropes, which are obtained in work-up by distillation or directly in the TBA synthesis.

The TBA used can be obtained by reaction of isobutene or isobutene-containing hydrocarbon mixtures, in particular raffinate I or selectively hydrogenated cracked $C_4$, with water or come from other industrial processes in which TBA has not necessarily been produced by an addition reaction but is obtained as by-product or coproduct, for example in the synthesis of tert-butyl hydroperoxide or in epoxidations using tert-butyl hydroperoxide.

The process of the present invention for the dissociation of TBA will be described in more detail below by way of example, without the process of the present invention being restricted to these embodiments. A person skilled in the art will readily be able to adapt the appropriate process steps for the dissociation of other addition products of isoolefins.

The TBA content of the feed to the first dissociation reactor, which comprises fresh starting material and a TBA/water recycle stream, is preferably from 40 to 99% by mass, more preferably from 55 to 98% by mass. The TBA content of the feed of the first dissociation reactor includes all values and subvalues therebetween, especially including 45, 50, 55, 60, 65, 70, 75, 80, 85, 90 and 95% by mass.

The space velocity which is particularly advantageous in an individual case depends on the water content of the reaction mixture and to a large degree on the reaction temperature and the activity of the catalyst used and has to be determined individually for each catalyst.

The space velocity (LHSV) in liters of feed per liter of catalyst after swelling per hour is generally from 10 to 100 l/(l*h) at a reaction temperature of from 80 to 100° C., from 15 to 300 l/(l*h) at a reaction temperature of from 100 to 130° C. and up to 600 l/(l*h) at a reaction temperature of from 130 to 150° C. However, lower space velocities can also be chosen. The space velocity at 80 to 100° C. includes all values and subvalues therebetween, especially including 20, 30, 40, 50, 60, 70, 80 and 90 l/(l*h). The space velocity at 100 to 130° C. includes all values and subvalues therebetween, especially including 20, 30, 40, 50, 60, 70, 80, 90, 100, 120, 140, 160, 180, 200, 220, 240, 260 and 280 l/(l*h). The space velocity of 130 to 150° C. includes all values and subvalues therebetween, especially including 50, 100, 150, 200, 250, 300, 350, 400, 450, 500 and 550 l/(l*h).

The reactor output from the dissociation according to the present invention of TBA is preferably separated into isobutene, by-product, water and a TBA/water mixture which is recirculated to the reactor and has a water content of less than 20% by mass, preferably less than 18% by mass, and more preferably less than 10% by mass and particularly preferably from 3 to 9% by mass. The water content of the TBA/water mixture includes all values and subvalues between 0 and 20% by mass, especially including 1, 2, 3, 4, 5, 6, 8, 10, 12, 14, 16 and 18% by mass.

The output from the reactor is preferably worked up by separating off the major part of the isobutene from the reactor output as an isobutene/water azeotrope at the top of a first column. After separating off part of the water from the overhead product from the first column, e.g. by phase separation, virtually water-free isobutene can be obtained from it by azeotropic distillation in a second column, for example (16). In this way, an isobutene having a purity of greater than 97% by mass, preferably greater than 98% by mass, particularly preferably greater than 99% by mass and very particularly preferably greater than 99.9% by mass, with the maximum water content being less than 10 000 ppm, preferably less than 1000 ppm, particularly preferably less than 250 ppm and very particularly preferably less than 50 ppm, can be obtained using the process of the present invention. An isobutene-containing mixture comprising isobutene and water in the above mentioned concentrations is likewise subject matter of the present invention. The purity of the isobutene includes all values and subvalues therebetween, especially including 97.5, 98, 98.5, 99, 99.5, 99.6, 99.7, 99.8 and 99.9% by mass. The maximum water content of the isobutene includes all values and subvalues therebetween, especially including 10, 20, 30, 40, 50, 100, 150, 200, 250, 500, 750, 1000, 2000, 3000, 4000, 5000, 6000, 7000, 8000 and 9000 ppm.

$C_8$-hydrocarbons and longer-chain hydrocarbons which are present as by-products in the output from the reactor can be separated off from the isobutene-free bottom product from the first column (4), for example as overhead product in a third column (6). However, it is likewise possible to separate off the $C_8$-hydrocarbons and any longer-chain hydrocarbons present as by-products in the reactor output as bottom product in a fourth column (23) in which a side stream taken off in vapor or liquid form from the first column (4) is distilled.

It can be advantageous for the bottom product from the first column (4) or the third column (6) to be separated in a fifth column (9) into a mixture of water and TBA, which may contain isobutene, as overhead product and, as bottom product, water which may contain organic impurities, with the tert-butanol/water mixture being at least partly recirculated to the reactor for dissociation of tert-butanol. 2-Butanol which may be present as impurity in the bottom product from the first or third column can, for example, be separated off from the water separated off as bottom product by distillation in a further column or as side stream in the fifth, for example column (9).

The distillate (12) from the isobutene enrichment (4a) in column (4), which consists essentially of an isobutene/water azeotrope, can be worked up in various ways. In particular it can be condensed and transferred to a settling or separation vessel or alternatively be condensed directly in a settling or separation vessel having heat-exchange elements and subjected to a liquid/liquid separation. After the liquid/liquid separation, part of the organic liquid can be fed to a further column (16) at the top or in the upper part of the column to give virtually water-free isobutene (18) at the bottom and an isobutene/water azeotrope at the top of this column. This isobutene/water azeotrope can be returned to the liquid/liquid separation vessel.

To avoid large process streams, it can be advantageous for the reactor output before separation into various fractions in a first column or a fraction obtained from it after separation to be subjected to removal of part of the water present in the reactor output or in the fractions obtained, e.g. by pervaporation and/or vapor permeation by means of a membrane. Preference is given to all of the water present in the reactor output, except for the part which may be necessary to allow isobutene and $C_8$-hydrocarbons to be separated off by azeotropic distillation, being separated off. The separation of part of the water from the reactor output prior to separation into various fractions in a first column can also be achieved by phase separation in a separation or settling vessel. Likewise, it can be advantageous to separate off part of the water present from the reactor feed prior to entry into the reactor, from example from stream (1), stream (10) and/or the resulting mixed stream, by pervaporation and/or vapor permeation by means of a membrane.

The removal of water from these streams or fractions comprising mixtures which may comprise water, TBA, isobutene and $C_8$-hydrocarbons and possibly further organic components is carried out over membranes which are permeable to water but barely permeable or impermeable to the abovementioned organic substances.

The removal of the water with the aid of a membrane can be carried out by reverse osmosis (retentate and permeate are liquid), by pervaporation (liquid retentate, gaseous permeate) or by vapor permeation (retentate and permeate are gaseous). Separation by simultaneous pervaporation and vapor permeation is also possible. The removal of the water by means of a membrane according to the present invention is preferably carried out by pervaporation (liquid retentate, gaseous permeate).

To separate off water by reverse osmosis, pervaporation or vapor permeation, it is possible to use commercial hydrophilic membranes. These membranes can be polymer membranes or inorganic membranes.

In the process of the present invention, it is possible to use, for example, polymer membranes from the companies Sulzer Chemtech, CM-Celfa, GKSS or Sophisticated Systems (polyimide membrane). Types which can be used are, for example, Pervap 2200, Pervap 2201, Pervap 2202 or Pervap 2510 from Sulzer or the type 2S-DP-H018 from Sophisticated Systems. As inorganic membranes, mention may be made, for example, of the following: SMS (Sulzer Chemtech); Silica (Pervatech); NaA (Mitsui or Smart Chemical). It is also possible to use combinations of an inorganic membrane or inorganic support material and a polymer membrane or applied separation layer of polymer.

According to the present invention, the removal of water over the inorganic membranes is preferably carried out at a temperature of from 20 to 200° C., and that over polymer membranes is preferably carried out at a temperature of from 20 to 150° C. The removal of water is particularly preferably carried out at a temperature of from 60 to 140° C. over both types of membrane.

The process of the present invention is preferably carried out at a pressure of the mixture (liquid, gaseous or mixed phase) fed to the membrane unit of from 0.5 to 30 bar, preferably from 0.8 to 20 bar. The pressure on the permeate side of the membrane is preferably from 0.001 to 1 bar. The pressure of the mixture fed to the membrane unit includes all values and subvalues therebetween, especially including 1, 2, 3, 4, 5, 10, 15, 20 and 25 bar. The pressure on the permeate side includes all values and subvalues therebetween especially including 0.005, 0.01, 0.05, 0.1, 0.5, 0.6, 0.7, 0.8 and 0.9 bar.

In the case of polymer membranes, the differential pressure is preferably from 0.01 to 20 bar, and in the case of inorganic membranes it is preferably from 0.01 to 30 bar. The differential pressures are particularly preferably in the range from 1 to 5 bar. The differential pressure for polymer membranes includes all values and subvalues therebetween, especially including 0.05, 0.1, 0.5, 1, 2, 4, 6, 8, 10, 12, 14, 16 and 18 bar. The differential pressure for inorganic membranes includes all values and subvalues therebetween especially including 0.05, 0.1, 0.5, 1, 2, 4, 6, 8, 10, 12, 14, 16, 18, 20, 22, 24, 26 and 28 bar. The mass flow (kg of permeate per square meter of membrane surface per hour) is preferably from 0.1 to 10 kg/(m²h), particularly preferably from 1 to 8 kg/(m²h). The mass flow includes all values and subvalues therebetween, especially including 0.5, 1, 1.5, 2, 2.5, 3, 3.5, 4, 4.5, 5, 5.5, 6, 6.5, 7, 7.5, 8, 8.5, 9 and 9.5 kg/(m²h). The water separated off as permeate preferably has a content of organic constituents, in particular TBA, of less than 10% by mass, preferably less than 5% by mass and very particularly preferably from 3 to 0.05% by mass. The content of organic constituents includes all values and subvalues therebetween, especially including 0.005, 0.01, 0.05, 0.1, 0.5, 1, 2, 3, 4, 5, 6, 7, 8 and 9% by mass. Smaller values down to 0.001% by mass can also be achieved, but this is usually not necessary and also not economically viable.

The removal of water by pervaporation can, as described above, be employed at various points in the process. Suitable streams are, for example, the reaction mixture leaving the dissociation reactor or the recirculated TBA/water mixture from the azeotrope column (for example, column (9)). The reaction mixture leaving the dissociation reactor is, apart from the wastewater streams, the stream having the highest water content. A relatively large part of the water can therefore be separated off from it by a membrane process with the least energy input compared to other streams. Further possibilities may be found in the reactor feed. There, for example, part of the water present can be removed from, for example, one of the streams (1), (10) and/or the mixed stream by pervaporation and/or vapor permeation by means of a membrane. This makes it possible to achieve TBA contents of greater than 90% by mass, which allow a particularly high conversion in the reactor (system).

The overhead product (10) from the azeotrope column (9), which is recirculated to the reactor (2), has an approximately azeotropic composition, i.e. a water content of from about 20 to 12% by mass. The water content includes all values and subvalues therebetween, especially including 1, 2, 4, 6, 8, 10, 12, 14, 16 and 18% by mass. Use of a membrane process enables the water content of this to be reduced to values of less than 12% by mass, in particular from 1 to 10% by mass, so that particularly little water is introduced into the reactor, as a result of which the space-time yield in the dissociation reactor increases. In another variant of the arrangement shown in FIG. 2, the membrane process, for example, (21) can be utilized to dewater the water-containing stream, for example, (26) which is obtained as bottoms from the first separation column, for example, (4) and is partly recirculated to the reactor.

It is naturally also possible to separate off water at various points of the process by membranes, e.g. at both of the above mentioned places.

If water is removed by a membrane, two basic variants are possible:

a) All of the water of reaction, possibly with the exception of a small residue which is necessary for separating off $C_8$-hydrocarbons and isobutene by azeotropic distillation, is separated off.

b) Only part of the water of reaction is removed by a membrane process. In case (a), the TBA/water azeotrope column can be omitted.

A block diagram of a plant in which the process of the present invention can be carried out is shown in FIG. 1. The feed (mixture) (1) together with the TBA/water azeotrope or approximately azeotropic composition (10) is fed into the reactor (2). The reactor (2) can consist of a single reactor or a reactor system (see below). The reaction mixture (3) leaving the reactor (2) is fed into the column (4) consisting of (4a) and (4b). In column (4), (4a) represents an isobutene enrichment part, (4b) represents a drift part, as upper and lower part of the column, respectively. If desired, the reaction mixture (3) leaving the reactor (2) can be dewatered and thus largely freed of water of reaction before it is introduced into the column (4). In the simplest case, the dewatering module (21) used can be a decanter (separation or settling vessel) which separates any two-phase mixture formed into an organic liquid stream (3A) and an aqueous liquid stream (3B). Significantly more water can be separated off by a membrane process, which likewise produces an organic liquid stream (3A) and an aqueous liquid stream (3B). The organic liquid stream (3A) is introduced into the column (4) and the aqueous liquid stream (3B) is fed into column (9) for discharge and further purification of the water or is passed to direct disposal. As overhead product (12) from the column (4) (4a+4b), isobutene containing small amounts of water is separated off and is separated in the settling vessel (13) into an isobutene phase and a water phase. The water phase (19) can be fed into the column (9). Part of the isobutene phase is recirculated as recycle stream (14) to the top of the column (4), and the other part (15) is separated in a column (16) into pure isobutene (18) and a water/isobutene azeotrope (17) which is returned to the separation vessel (13). To improve the separation of the TBA from the isobutene in column (4), a fresh water stream (20) can optionally be added at the top or in the enrichment section (4a) of the column (4). The bottom product (5) of the column (4) is passed to column (6) where $C_8$-hdyrocarbons are taken off as overhead product (7). The bottom product (8) is separated in column (9) into water which possibly contains organic components (e.g. 2-butanol and/or $C_{12}$-hydrocarbons) (11) and a TBA/water azeotrope (10) which may contain small amounts of isobutene (from stream (19)). Stream (10) is recirculated to the reactor (2). Any organic components (e.g. 2-butanol (SBA) and/or $C_{12}$-hydrocarbons) present in the wastewater stream (11) can easily be separated off from pure water by distillation. As an alternative, 2-butanol can be discharged in a targeted fashion by taking off a stream from the vapor phase of the vaporizer of the column or a gaseous or liquid stream from the stripping section of the column (9) as side stream (11A).

A block diagram of an alternative plant in which the process of the present invention can be carried out is shown in FIG. 2. The feed (mixture) (1) together with the TBA/water azeotrope or approximately azeotropic composition (10) is fed into the reactor (2). The reactor (2) can consist of a single reactor or a reactor system (see below). The reaction mixture (3) leaving the reactor (2) is fed into the column (4) consisting of isobutene enrichment part (4a) and drift part (4b). If desired, the reaction mixture (3) leaving the reactor (2) can be dewatered and thus largely freed of water of reaction before it is introduced into the column (4). In the simplest case, the dewatering module (21) used can be a decanter (separation or settling vessel) which separates any two-phase mixture formed into an organic liquid stream (3A) and an aqueous liquid stream (3B). Significantly more water can be separated off by a membrane process, which likewise produces an organic liquid stream (3A) and an aqueous liquid stream (3B). The organic liquid stream (3A) is introduced into the column (4) and the aqueous liquid stream (3B) is fed into column (9) for discharge and further purification of the water or is passed to direct disposal. As overhead product (12) from the column (4), isobutene containing small amounts of water is separated off and is separated in the settling vessel (13) into an isobutene phase and a water phase. The water phase (19) can be fed into the column (9). Part of the isobutene phase is recirculated as recycle stream (14) to the top of the column (4), and the other part (15) is separated in a column (16) into pure isobutene (18) and a water/isobutene azeotrope (17) which is returned to the separation vessel (13). To improve the separation of the TBA from the isobutene in column (4), a fresh water stream (20) can optionally be added at the top or in the enrichment section of the column (4). The bottom product (5) is separated in column (9) into water which possibly contains organic components (e.g. 2-butanol and/or $C_{12}$-hydrocarbons) (11) and a TBA/water azeotrope (10) which may contain small amounts of isobutene (from stream (19)). Stream (10) is recirculated to the reactor (2). All or part of the vapor (27) from the column (9) can be introduced into column (4) in order to save energy and adjust the concentration. A part (26) of the bottom stream (5) can be fed directly to the reactor. Any organic components (e.g. 2-butanol and/or $C_{12}$-hydrocarbons) present in the wastewater stream (11) can easily be separated off from pure water by distillation. To separate off $C_8$-hydrocarbons, a gaseous or liquid side stream (22) is taken from the column (4) and passed to column (23) where the $C_8$-hydrocarbons together with TBA and water are taken off as bottom product (24). Isobutene and TBA are recovered as overhead product (25) and are returned to the column (4).

A further possible option is firstly to introduce the feed stream (1) into one or more further reactor(s) and to feed the prereacted mixture into column (4a).

The fractional distillation of streams obtained in the process of the present invention can be carried out in one or more columns containing internals which may comprise trays, rotating internals, random and/or ordered beds or packing. The separation of the isobutene from the reactor output by distillation is preferably carried out in a single column.

Examples of types of column internals which can be used are:

Trays having holes or slots in the baseplate.

Trays with necks or chimneys covered by bubble caps, caps or hoods.

Trays having holes in the baseplate which are covered by movable valves.

Trays having special construction.

In columns having rotating internals, the runback is either sprayed by means of rotating funnels or spread as a film over a heated wall by means of rotor.

Irregular beds of various packing elements can also be employed in columns used in the process of the present invention. The packing elements can consist of virtually any materials, e.g. steel, stainless steel, copper, carbon, stoneware, porcelain, glass, plastics, etc., or mixtures thereof, and have various shapes, e.g. spheres, rings with smooth or profiled surfaces, rings with internal struts or holes through the wall, wire mesh rings, saddles or spirals.

Packing having a regular geometry can, for example, consist of metal or plastic sheets or mesh. Examples of such types of packing are Sulzer mesh packing BX, Sulzer lamellar packing Mellapak made of sheet metal, high-performance packing such as MellapakPlus, structured packing from Sulzer (Optiflow), Montz (BSH) and Kuhni (Rombopak).

The operating pressure in the columns used in the process of the present invention, in particular, for example, the columns (4), (6), (9), (16) and (23), is preferably in the range from 0.5 to 15 $bar_{abs}$ (bara), particularly preferably from 1 to 10 bara. The operating pressure includes all values and subvalues therebetween, especially including 1, 2, 3, 4, 5, 6, 7, 8, 9, 10, 11, 12, 13, and 14 bara.

The column (4) used for separation of the reactor output preferably has from 5 to 80 theoretical plates, more preferably from 10 to 60 theoretical plates. The number of theoretical plates includes all values and subvalues therebetween, especially including 10, 15, 20, 25, 30, 35, 40, 45, 50, 55, 60, 65, 70 and 75. The feed plate depends on the composition of the feed. It has been found to be advantageous for the reactor output to be fed in on the 4th to 55th theoretical plate counted from the top, in particular the 5th to 50th theoretical plate, in the lower section of the column, in particular the isobutene enrichment part (4a) of FIG. 1 and FIG. 2. The fresh water (21) is fed in at the top of the column (4) on plate 1. This likewise applies to the runback (14). The optional vapor stream (27) from the column (9) is fed in at the bottom of the column (4).

In a particular embodiment of the present invention of the type shown in FIG. 2, it has been found to be advantageous for the gaseous or liquid stream (22) to be taken off at the 4th to 65th theoretical plate counted from the top, in particular the 5th to 60th theoretical plate, of the column (4) of FIG. 2. The isobutene-rich stream (25) is fed back in at the same point or preferably a higher point (higher up in the column: isobutene enrichment part (4a), i.e. on the 2nd to 65th theoretical plate counted from the top, in particular the 3rd to 60th theoretical plate, of the column (4) of FIG. 2.

The column (9) used for discharging the wastewater and concentrating the TBA preferably has from 5 to 70 theoretical plates, more preferably from 8 to 65 theoretical plates. The number of theoretical plates includes all values and subvalues therebetween, especially including 10, 15, 20, 25, 30, 35, 40, 45, 50, 55, 60, and 65. The feed plate depends on the composition of the feed. It has been found to be advantageous for the stream (5) in FIG. 2 or the stream (8) in FIG. 1 to be fed in on the 1st to 55th theoretical plate counted from the top, in particular the 1st to 45th theoretical plate. The possible wastewater (3B) and (19) is fed in on the 1st to 60th theoretical plate counted from the top, in particular the 1st to 50th theoretical plate.

The column (16) used for drying the isobutene preferably has from 4 to 35 theoretical plates, more preferably from 5 to 30 theoretical plates. The number of theoretical plates includes all values and subvalues therebetween, especially including 10, 15, 20 and 25. It has been found to be advantageous for the feed (15) to be fed in on the 1st to 6th theoretical plate counted from the top, in particular on the 1 st to 4th theoretical plate.

The column (6) used in FIG. 1 for discharging $C_8$-hydrocarbons preferably has from 4 to 75 theoretical plates, more preferably from 5 to 50 theoretical plates. The number of theoretical plates includes all values and subvalues therebetween, especially including 10, 15, 20, 25, 30, 35, 40, and 45. The feed plate depends on the composition of the feed. It has been found to be advantageous for the stream (5) in FIG. 1 to be fed in on the 1st to 55th theoretical plate counted from the top, in particular the 1 st to 45th theoretical plate.

The column (23) used in FIG. 2 for discharging $C_8$-hydrocarbons preferably has from 4 to 65 theoretical plates, more preferably from 5 to 50 theoretical plates. The number of theoretical plates includes all values and subvalues therebetween, especially including 10, 15, 20, 25, 30, 35, 40, and 45. It has been found to be advantageous for the feed (22) to be fed in on the 1st to 25th theoretical plate counted from the top, in particular on the 1st to 15th theoretical plate. The product stream (25) is taken off as distillate at the top of the column, either in gaseous or liquid form, preferably in gaseous form.

Customary components such as pumps, compressors, valves, heat exchangers and vaporizers are not found in the block diagrams, but these are self-evident components of a plant.

A particular feature of the reactor system for carrying out equilibrium reactions isothermally in the liquid phase over fixed-bed catalysts, where at least one of the reaction products is partly, preferably predominantly, present in gaseous form under temperature and pressure conditions under which all starting materials and at least one reaction product are predominantly present in liquid form, in particular for carrying out the process of the present invention, is that the reactor system has at least two physically separate reaction zones which each have a catalyst arranged in a fixed bed and facilities for maintaining isothermal operation, where between each two reaction zones there is a separation zone having means for bringing at least part of at least one of the products of the equilibrium reaction into the gas phase by changing the pressure or temperature, separating it off from the reaction mixture and discharging it from the reactor and for transferring the remaining reaction mixture to the following reaction zone, with a further means which enables the temperature or pressure in the subsequent reaction zone to be set to precisely the value in the preceding reaction zone being able to be present if desired. The means of setting the temperature can be, for example, customary plates or tube heat exchangers. The means of bringing at least one of the products of the equilibrium reaction into the gas phase can likewise be a heat exchanger, so that this reaction product is vaporized by introduction of thermal energy into the reaction mixture. It is likewise possible for the means to be a kettle vaporizer or a heated vessel which enables the pressure to be decreased when the reaction mixture enters the separation zone. In such a reactor design, the pressure of the reaction mixture as it enters the reaction zone following the separation zone is lower than in the preceding reaction zone.

Having generally described this present invention, a further understanding can be obtained by reference to certain specific examples which are provided herein for purposes of illustration only, and are not intended to be limiting unless otherwise specified.

EXAMPLES

Example 1

Prophetic Example

The preparation of isobutene is carried out in a plant of the type shown in FIG. 1 and FIG. 5, with the particular feature that no removal of water using the module (21) is carried out and the streams 3 and 3A therefore has the same composition. The fresh water stream (20) and the wastewater stream (3B) are dispensed with. The wastewater stream (19) is disposed of directly.

The reaction section (2) is in two stages as shown in FIG. 5. The reactor (29) is a laboratory tube reactor operated isothermally at 120° C. and having a catalyst volume of about 310 ml. Amberlyst 15 is used as catalyst. The second reactor (35) is likewise a laboratory tube reactor operated isothermally at 120° C. and having a catalyst volume of about 310 ml. Amberlyst 15 is likewise used as catalyst. A heatable vessel is used for intermediate vaporization.

The diameter of the columns (4), (6), (9) and (16) is in each case 50 mm. Random metal packing elements are used. About 30 theoretical plates are installed in column (4), and the reactor output (3) is fed in on the 20th theoretical plate counted from the top. The runback (14) is introduced at the top of the column on plate 1. About 18 theoretical plates are installed in column (6), and the feed (5) from column (4) is fed in on the 12th theoretical plate counted from the top. About 13 theoretical plates are installed in column (9), and the feed (8) from column (6) is fed in on the 2nd theoretical plate counted from the top. The side stream (11A) is taken off in vapor form at approximately the 10th theoretical plate, counted from the top.

The feed (1) used for the experiments is taken from an industrial plant for the preparation of isobutene and had the composition shown in Table 1. Some $C_8$-hydrocarbons and other high boilers are already present in small amounts in the feed and further amounts of them are formed in the dissociation of the TBA in the reactor system. The stream numbers in the following table correspond to those in FIG. 1, and those in the reaction section correspond to those in FIG. 5. Components present in a concentration of less than 0.1 parts by mass in the mixture are generally not reported in the Table.

TABLE 1

| Stream number | Stream name | Mass flow [kg/h] | Concentration of components in parts by mass |
|---|---|---|---|
| 1 | Fresh feed | 2.5 | 9.4 water |
|   |   |   | 90.5 TBA |
|   |   |   | 0.1 SBA (2-butanol) |
| 3 | Total reactor output | 7.891 | 21.4 isobutene |
|   |   |   | 21.4 water |
|   |   |   | 57.0 TBA |
|   |   |   | 0.2 SBA |
| 5 | Bottoms from column (4) | 6.187 | 27.1 water |
|   |   |   | 72.7 TBA |
|   |   |   | 0.2 SBA |
| 7 | Distillate from column (6) | 0.003 | 13.0 water |
|   |   |   | 58.2 TBA |
|   |   |   | 28.8 $C_8$ |
| 8 | Bottoms from column (6) | 6.185 | 27.1 water |
|   |   |   | 72.7 TBA |
|   |   |   | 0.2 SBA |

TABLE 1-continued

| Stream number | Stream name | Mass flow [kg/h] | Concentration of components in parts by mass |
|---|---|---|---|
| 10 | Distillate from column (9) | 5.391 | 17.0 water<br>82.8 TBA<br>0.2 SBA |
| 11A | Side stream taken from column (9) | 0.04 | 21.3 water<br>74.9 TBA<br>3.7 SBA<br>0.1 other components |
| 11 | Bottoms from column (9) | 0.754 | 99.995 water<br>0.005 other components |
| 12 | Distillate from column (4) | 2.503 | 99.3 isobutene<br>0.6 water |
| 14 | External runback to column (4) | 0.8 | 99.9 isobutene<br>0.1 water |
| 15 | Feed to column (16) | 1.986 | 99.9 isobutene<br>0.1 water |
| 17 | Distillate from column (16) | 0.297 | 99.5 isobutene<br>0.5 water |
| 18 | Bottoms from column (16) | 1.689 | 99.96 isobutene<br>0.04 other components |
| 19 | Wastewater from separation vessel (13) | 0.015 | 99.9 water<br>0.1 TBA |
| 28 | Feed to reactor (29) | 7.891 | 14.6 water<br>85.2 TBA<br>0.2 SBA |
| 31 | Vapor phase separated off (30) | 1.13 | 61.5 isobutene<br>8.5 water<br>30.0 TBA<br>0.1 SBA |
| 36 | Output from reactor (35) | 6.76 | 14.7 isobutene<br>23.6 water<br>61.5 TBA<br>0.2 SBA |
| 37 | Output from reactor (29) | 7.891 | 17.3 isobutene<br>20.1 water<br>62.4 TBA<br>0.2 SBA |

The pressure in the reactor (29) is 19 bar$_{abs.}$, the pressure in the reactor (35) is 18 bar$_{abs.}$, and the intermediate vaporization (38) is carried out at 15 bar$_{abs.}$. The columns (4), (6), (9) and (16) are each operated at a pressure of about 6 bar$_{abs.}$ at the top. Column (4) is equipped with a dephlegmator and operated using a runback stream of about 11.5 kg/h. A space-time yield of 2.7 kg/(l*h) based on the total amount of catalyst used is obtained.

Example 2

Prophetic Example

The preparation of isobutene is carried out in a plant of the type shown in FIG. 1, with the particular feature that no removal of water by means of the module (21) is carried out and the streams 3 and 3A therefore have the same composition. The fresh water stream (20) and the wastewater stream (3B) are dispensed with. The wastewater stream (19) is disposed of directly.

The reaction section (2) is configured as a single stage. The reactor (2) is a laboratory tube reactor operated isothermally at 120° C. and having a catalyst volume of about 285 ml. Amberlyst 15 is used as catalyst. The diameter of the columns (4), (6), (9) and (16) is in each case 50 mm. Metal packing elements (Pall rings) are used in each case. About 30 theoretical plates are installed in column (4), and the reactor output (3) is fed in on the 20th theoretical plate counted from the top. The runback (14) is introduced at the top of the column on plate 1. About 18 theoretical plates are installed in column (6), and the feed (5) from column (4) is fed in on the 12th theoretical plate counted from the top. About 13 theoretical plates are installed in column (9), and the feed (8) from column (6) is fed in on the 2nd theoretical plate counted from the top. The side stream (11A) is taken off in gaseous form at about the 10th theoretical plate, counted from the top.

The feed (1) used for the experiments is taken from an industrial plant for the preparation of isobutene and has the composition shown in Table 2. Some $C_8$-hydrocarbons and other high boilers are already present in small amounts in the feed and further amounts of them are formed in the dissociation of the TBA in the reactor system. The stream numbers in the following table correspond to those in FIG. 1. Components present in a concentration of less than 0.1 parts by mass in the mixture are generally not reported in the Table.

TABLE 2

| Stream number | Stream name | Mass flow [kg/h] | Concentration of components in parts by mass |
|---|---|---|---|
| 1 | Fresh feed | 2.5 | 9.4 water<br>90.5 TBA<br>0.1 SBA |
| 3 | Reactor output | 9.756 | 17.3 isobutene<br>20.1 water<br>62.4 TBA<br>0.2 SBA |
| 5 | Bottoms from column (4) | 7.988 | 23.6 water<br>76.2 TBA<br>0.2 SBA |
| 7 | Distillate from column (6) | 0.004 | 3.3 isobutene<br>12.5 water<br>65.2 TBA<br>19.1 $C_8$ |
| 8 | Bottoms from column (6) | 7.984 | 23.6 water<br>76.2 TBA<br>0.2 SBA |
| 10 | Distillate from column (9) | 7.256 | 16.4 water<br>83.4 TBA<br>0.2 SBA |
| 11A | Side stream taken off from column (9) | 0.040 | 22.7 water<br>73.6 TBA<br>3.7 SBA<br>0.1 other components |
| 11 | Bottoms from column (9) | 0.688 | 99.995 water<br>0.005 other components |
| 12 | Distillate from column (4) | 2.568 | 96.8 isobutene<br>3.2 water |
| 14 | External runback to column (4) | 0.800 | 99.9 isobutene<br>0.1 water |
| 15 | Feed to column (16) | 1.988 | 99.9 isobutene<br>0.1 water |
| 17 | Distillate from column (16) | 0.300 | 99.5 isobutene<br>0.5 water |
| 18 | Bottoms from column (16) | 1.688 | 99.965 isobutene<br>0.045 other components |
| 19 | Wastewater from separation vessel (13) | 0.081 | 99.9 water<br>0.1 TBA |

The pressure in the reactor (2) is 19 bar$_{abs.}$. The columns (4), (6), (9) and (16) are operated at a pressure of about 6 bar$_{abs.}$ at the top. Column (4) is equipped with a dephlegmator and operated using a runback stream of about 5.1 kg/h. A space-time yield of 5.8 kg/(l*h) based on the total amount of catalyst used is obtained.

The examples impressively demonstrate how the circulated streams through the reactor can be reduced in the novel plant for preparing isobutene. DE 3151446 gives examples in which the ratio of the mass flows of fresh feed to circulated streams is reported as from 1:7.4 to 1:16.6 (see Table 1 in that document), while Example 2 achieves a ratio of the mass flows of fresh feed (1) to recycle stream (10) of 1:2.9 and Example 1 achieves a ratio of 1:2.16 as a result of the higher partial conversion in the reactor system. These values can be improved further by, for example, increasing the degree of concentration to the TBA/water azeotrope in column (9).

German patent application 10327215.1 filed Jun. 17, 2003, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing isobutene, comprising:
dissociating tert-butanol into isobutene and water over an acid ion-exchange resin arranged as a fixed bed in at least one reactor at a temperature of from 80 to 150° C. and at a pressure of from 5 to 25 bar to obtain a reaction mixture,
separating the reaction mixture into isobutene, a by-product, water and at least one mixture of undissociated tert-butanol and water;
wherein the reactor is operated pseudo-isothermally, with a temperature difference between inflowing and outflowing streams of less than 15 K;
wherein the dissociation is carried out to the equilibrium of the dissociation reaction in a first reaction zone, isobutene is separated off in gaseous form in a subsequent separation zone and the dissociation is continued to the equilibrium of the dissociation reaction in a subsequent reaction zone, and, if further separation zones and reaction zones are present, these process steps are repeated at least one time.

2. The process as claimed in claim 1, wherein a feed to the reactor comprises a fresh feed stream and one or more recycle streams which comprise a mixture of undissociated tert-butanol, water and optionally a by-product, wherein a mass ratio of fresh feed stream to the sum of the recycle streams is less than 1:10.

3. The process as claimed in claim 1, wherein a plurality of reactors connected in series or in parallel are used and all reactors are operated isothermally.

4. The process as claimed in claim 1, wherein the pressure and the temperature in the reaction zones of the reactor are chosen so that the reaction mixture is present in the liquid phase and the pressure and the temperature in the separation zones are chosen so that part of the isobutene is present in the gas phase.

5. The process as claimed in claim 1, wherein the process is carried out in at least two reactors and a liquid reactor output from a first reactor is passed to a zone in which part of the reactor output is brought into a gas phase by changing the pressure and/or temperature and is separated off from the liquid phase and the liquid phase is passed to a second reactor.

6. The process as claimed in claim 1, wherein an intermediate vaporization in a two-stage or multistage reactor system is carried out by reducing the pressure to below the pressure of the dissociation.

7. The process as claimed in claim 1, wherein, in a vaporization in a two-stage or multistage reactor system, heat exchange is carried out between a liquid stream fed to a vaporization and a liquid stream returned from the vaporization.

8. The process as claimed in claim 1, wherein a reactor output is separated into isobutene, a by-product, water and a tert-butanol/water mixture which has a water content of less than 10% by mass and is recirculated to the reactor.

9. The process as claimed in claim 1, wherein a major part of the isobutene is separated off from a reactor output as an isobutene/water azeotrope at a top of a first column.

10. The process as claimed in claim 1, wherein a part of the water is separated off from an overhead product from a first column by phase separation and a virtually water-free isobutene is then isolated by azeotropic distillation in a second column.

11. The process as claimed in claim 1, wherein $C_8$-hydrocarbons and longer-chain hydrocarbons which are present as by-products in an output from the reactor are separated off from an isobutene-free bottom product from a first column as overhead product in a third column.

12. The process as claimed in claim 1, wherein $C_8$-hydrocarbons and optionally longer-chain hydrocarbons which are present as by-products in an output from the reactor are separated off as bottom product in a fourth column in which a gaseous or liquid side stream taken off from a first column is distilled.

13. The process as claimed in claim 1, wherein a bottom product from a first column or a third column is separated off in a fifth column into a mixture of water and tert-butanol, which may contain isobutene, as overhead product and, as bottom product, water which may contain organic impurities, with the tert-butanol/water mixture being at least partly recirculated to the reactor for dissociation of tert-butanol.

14. The process as claimed in claim 13, wherein 2-butanol is separated off by distillation from the water which has been separated off as bottom product or is separated off as side stream in the fifth column.

15. The process as claimed in claim 1, wherein a distillate from an isobutene enrichment part of a first column, which comprises an isobutene/water azeotrope, is condensed and transferred to a settling or separation vessel; or
alternatively said distillate is condensed directly in a settling or separation vessel having heat-exchange elements; and
after the liquid/liquid separation, part of the organic liquid is fed to a column at the top or in the upper part of the column to give virtually water-free isobutene at the bottom and an isobutene/water azeotrope at the top of this column, with the isobutene/water azeotrope being returned to the liquid/liquid separation vessel.

16. The process as claimed in claim 1, wherein part of the water present in an output from the reactor is separated off from the latter by pervaporation and/or vapor permeation by a membrane before the reactor output is separated into various fractions in a first column.

17. The process as claimed in claim 1, wherein part of the water present is separated off from a reactor feed prior to entry into the reactor by pervaporation and/or vapor permeation using a membrane.

18. The process as claimed in claim 1, wherein part of the water present in an output from the reactor is separated off by separation in a separation or settling vessel before an output from the reactor is separated into various fractions in a first column.

19. The process as claimed in claim 18, wherein all of the water of reaction, except for the part which may be necessary to allow isobutene and $C_8$-hydrocarbons to be separated off by azeotropic distillation, is separated off.

20. The process as claimed in claim 1, wherein isobutene is obtained in a purity of at least 99% by mass, with the maximum water content being less than 250 ppm.

* * * * *